United States Patent [19]

Plöger et al.

[11] 3,957,160

[45] May 18, 1976

[54] PROCESS FOR THE PREVENTION OF PRECIPITATIONS IN WATER OR AQUEOUS SOLUTIONS

[75] Inventors: Walter Plöger, Hilden; Karl-Heinz Worms, Dusseldorf-Holthausen, both of Germany

[73] Assignee: Henkel & Cie G.m.b.H., Dusseldorf-Holthausen, Germany

[22] Filed: Jan. 26, 1972

[21] Appl. No.: 221,041

[30] Foreign Application Priority Data

Feb. 1, 1971 Germany............................ 2104476

[52] U.S. Cl.................................. 210/58; 252/180
[51] Int. Cl.$^2$........................................ C02B 5/06
[58] Field of Search......................... 210/58, 54, 59; 252/180; 260/502.4

[56] References Cited

UNITED STATES PATENTS

| 3,303,139 | 2/1967 | Blaser et al. | 252/180 |
| 3,617,576 | 11/1971 | Kerst | 210/58 |
| 3,668,138 | 6/1972 | Hoover et al. | 252/180 |

*Primary Examiner*—Charles N. Hart
*Assistant Examiner*—Peter A. Hruskoci
*Attorney, Agent, or Firm*—Hammond & Littell

[57] ABSTRACT

The invention relates to a process for the prevention of inorganic salt precipitations in water or aqueous solutions by the additions to the solutions of small amounts of N-substituted aminoalkane-1,1-diphosphonic acids or their alkali metal salts or ammonium salts.

3 Claims, No Drawings

PROCESS FOR THE PREVENTION OF PRECIPITATIONS IN WATER OR AQUEOUS SOLUTIONS

BACKGROUND OF THE INVENTION

It is often desirable in today's technology to prevent precipitation of alkaline earth salts or of iron salts from water or aqueous solutions. For this purpose inorganic and organic sequestering agents have previously been proposed and utilized. For instance, the organic compounds nitrilo triacetic acid or ethylenediamine tetraacetic acid have been used. Likewise polymeric phosphates have also been used as sequestering agents. The latter have the advantage that they can prevent precipitation even if applied in less than a stoichiometric amount. The disadvantages of the polymeric phosphates, however, are that they lose effectiveness at elevated temperatures and that they readily hydrolyze, particularly in the acidic pH-range. For reasons related to sewage disposal, additional problems may develop in the use of phosphates. It has already been proposed to use organic phosphonic acids, such as non-substituted aminotrimethylene phosphonic acid, for this purpose, but it has been found that corrosion problems occur therefrom.

OBJECTS OF THE INVENTION

It is an object of the present invention to provide a process for inhibiting the precipitation of insoluble salts from aqueous solutions comprising adding to an aqueous solution containing a precipitable salt, a sequestering agent selected from the group consisting of (a) N-substituted aminoalkane-1,1-diphosphonic acids, (b) alkali metal salts of said acids, (c) ammonium salts of said acids, and (d) mixtures thereof in a molar ratio of $5 \times 10^{-4}$ to $5 \times 10^{-2}$ mols of said agent per mol of precipitatable salt cation in said aqueous solution.

It is a further object of the present invention to provide a process for inhibiting the precipitation of insoluble salts from aqueous solutions comprising adding to an aqueous solution containing a precipitable salt, a sequestering agent selected from the group consisting of (a) N-substituted aminoalkane-1,1-diphosphonic acids having the formula

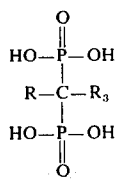

wherein $R_3$ is a member selected from the group consisting of hydrogen, alkyl having 1 to 4 carbon atoms, and phenyl; and wherein R is a member selected from the group consisting of piperidino, morpholino, pyrrolidono, piperazino, and

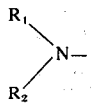

wherein $R_1$ is a member selected from the group consisting of alkyl having 1 to 6 carbon atoms, phenyl, phenylalkyl having 7 to 9 carbon atoms, alkylphenyl having 7 to 9 carbon atoms, cycloalkyl having 5 to 6 carbon atoms, pyridyl, and pyrrolyl; and wherein $R_2$ is a member selected from the group consisting of hydrogen and alkyl having 1 to 6 carbon atoms, (b) alkali metal salts of said acids, (c) ammonium salts of said acids, and (d) mixtures thereof in a molar ratio of $5 \times 10^{-4}$ to $5 \times 10^{-2}$ mols of said agent per mol of precipitable salt cation in said aqueous solution.

Further objects of the present invention will become apparent as the description thereof proceeds.

DESCRIPTION OF THE INVENTION

The present invention is directed to a process for inhibiting the precipitation of insoluble salts from aqueous solutions comprising adding to an aqueous solution containing a precipitable salt, a sequestering agent selected from the group consisting of (a) N-substituted aminoalkane-1,1-diphosphonic acids, (b) alkali metal salts of said acids, (c) ammonium salts of said acids, and (d) mixtures thereof in a molar ratio of $5 \times 10^{-4}$ to $5 \times 10^{-2}$ mols of said agent per mol of precipitable salt cation in said aqueous solution.

The present invention also provides a process for inhibiting the precipitation of insoluble salts from aqueous solutions comprising adding to an aqueous solution containing a precipitable salt, a sequestering agent selected from the group consisting of (a) N-substituted aminoalkane-1,1-diphosphonic acids having the formula

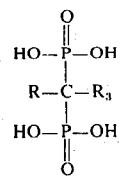

wherein $R_3$ is a member selected from the group consisting of hydrogen, alkyl having 1 to 4 carbon atoms, and phenyl; and wherein R is a member selected from the group consisting of piperidino, morpholino, pyrrolidino, piperazino, and

wherein $R_1$ is a member selected from the group consisting of alkyl having 1 to 6 carbon atoms, phenyl, phenylalkyl having 7 to 9 carbon atoms, alkylphenyl having 7 to 9 carbon atoms, cycloalkyl having 5 to 6 carbon atoms, pyridyl, and pyrrolyl; and wherein $R_2$ is a member selected from the group consisting of hydrogen and alkyl having 1 to 6 carbon atoms, (b) alkali metal salts of said acids, (c) ammonium salts of said acids, and (d) mixtures thereof in a molar ratio of $5 \times 10^{-4}$ to $5 \times 10^{-2}$ mols of said agent per mol of precipitable salt cation in said aqueous solution. These precipitable salt cations are usually based on alkaline earth and/or iron cations.

Readily available N-substituted aminoalkane-1,1-diphosphonic acids are as follows but they are not to be deemed limitative of the present invention in any manner:

N-methyl-1-aminomethane-1,1-diphosphonic acid
N,N-dimethyl-1-aminomethane-1,1-diphosphonic acid
N-ethyl-1-aminomethane-1,1-diphosphonic acid
N,N-diethyl-1-aminomethane-1,1-diphosphonic acid
N-butyl-1-aminomethane-1,1-diphosphonic acid
N,N-dibutyl-1-aminomethane-1,1-diphosphonic acid
N-pentyl-1-aminomethane-1,1-diphosphonic acid
N-hexyl-1-aminomethane-1,1-diphosphonic acid
N-benzyl-1-aminomethane-1,1-diphosphonic acid
N-cyclohexyl-1-aminomethane-1,1-diphosphonic acid
N-(4-pyridyl)-1-aminomethane-1,1-diphosphonic acid
N,N-dimethyl-1-aminoethane-1,1-diphosphonic acid
N,N-dimethyl-1-aminobutane-1,1-diphosphonic acid
N-(2,4,6-trimethylphenyl)-1-aminomethane-1,1-diphosphonic acid.

Other substituted aminoalkane-1,1-diphosphonic acids which are preferable are those in which the nitrogen atom of the substituted amino group is also the nitrogen atom of a heterocyclic 5 or 6 membered ring. The heterocyclic ring can contain other hetero atoms, such as particularly oxygen or nitrogen. Preferably compounds such as piperidino-methane-1,1-diphosphonic acid and morpholinomethane-1,1-diphosphonic acid are of interest, as well as pyrrolidino and piperazino compounds.

The preparation of the applicable phosphonic acids can, for example, be carried out by reaction of phosphorus trihalides with monocarboxylic acid amides, followed by hydrolyzation of the reaction products. The acids can optionally be transformed to the alkali metal salts or ammonium salts by a suitable neutralization. The preparation of these compounds is not the object of the present patent application.

The N-substituted aminoalkane-1,1-diphosphonic acids or their alkali metal salts or ammonium salts, to be utilized as precipitation prevention agents can be added in solid form but are preferably added in the form of aqueous solutions to the water system or to the aqueous system to be protected from precipitation. The amount of the agent added depends upon the amount of the alkaline earth cations and/or iron cations contained in the aqueous system. These agents are usually added to the solution in an effective amount to produce a molar range of $5 \times 10^{-4}$ to $5 \times 10^{-2}$ mols of agent per one mol of cation to be prevented from precipitating. An unexpected result is that such slight amounts of added inhibitors can effectively prevent undesired precipitations in water or aqueous systems. This effectiveness is furthermore obtainable at elevated temperatures, particularly above 40°C. It has additionally been found that no corrosion problems arise when the thusly treated aqueous systems containing these acid agents are brought into contact with metals such as iron and particularly aluminum, in the form of pipes, tanks, etc.

The following examples are not to be deemed limitative of the invention in any manner.

EXAMPLE 1

In each of the following tests the procedure was first to prepare an aqueous solution of a highly soluble salt of an alkaline earth metal cation. A second aqueous solution was prepared containing a soluble salt, the anion of which will react with the alkaline earth metal cation of the first solution to form a relatively insoluble alkaline earth salt. The inhibitor of the present invention is added to either the first or the second solutions, and both solutions are then mixed to form a mixture. The concentration of the first and second solutions were chosen so that the solubility limit of the insoluble alkaline earth compound formed in the mixture was surpassed several times. As a control in each experiment a blank test mixture without the addition of the inhibitor was prepared.

30 ml of a 0.1 molar $CaCl_2$ solution (corresponding to 3 m mols of $Ca^{++}$ = 100%) were treated with an amount, designated in Table I as $x$ in milliliter of a 1.5 m mol/liter solution of the inhibitor. Subsequently $940-x$ ml of freshly boiled, degassed distilled water were added. Then 30 ml of a 0.1 molar $Na_2CO_3$-solution were added.

The blank test was prepared analogously, but without an addition of inhibitor.

Both samples were allowed to stand for 24 hours at 20°C. In the blank test a precipitate of calcium carbonate had formed. In the sample containing an inhibitor there was no precipitate or a substantially lesser amount of precipitate, as shown in Table I.

From both samples aliquot amounts were taken and in each case the concentration of dissolved calcium in the total sample was determined by titration. The determination was carried out in the blank test directly with the solution and in the inhibited sample after treatment with an ion exchange resin to remove the inhibitor. The total amount of calcium used was made equal to 100%; and the concentrations found in the samples were calculated and are set forth in the following table.

Table I

Inhibition of the formation of a $CaCO_3$-precipitate by N-substituted aminoalkane-1,1-diphosphonic acids after 24 hours at 20°C

| Inhibitor NO. | Inhibitor | Inhibitor amount × ml | Relative Molar Concentration of $Ca^{++}$ : Inhibitor | Ca-dissolved in % of total Ca |
|---|---|---|---|---|
| 1 | N-Cyclohexylaminomethanediphosphonic acid | 6 | 1000 : 3 | 100 |
|  |  | 20 | 100 : 1 | 100 |
| 2 | N-(4-Pyridyl)-aminomethanediphosphonic acid | 6 | 1000 : 3 | 100 |
|  |  | 20 | 100 : 1 | 100 |
| 3 | N-Hexylaminomethanediphosphonic acid | 6 | 1000 : 3 | 100 |
|  |  | 20 | 100 : 1 | 100 |
| 4 | N-Methyl-1-aminoethanediphosphonic acid | 2 | 1000 : 1 | 76.5 |
|  |  | 4 | 1000 : 2 | 100 |
|  |  | 6 | 1000 : 3 | 100 |
|  |  | 20 | 100 : 1 | 100 |
| 5 | N-Ethylaminomethanediphosphonic acid | 6 | 1000 : 3 | 100 |
|  |  | 20 | 100 : 1 | 100 |
| 6 | Morpholino-N-methanediphosphonic acid | 2 | 1000 : 1 | 48 |
|  |  | 6 | 1000 : 3 | 100 |
|  |  | 20 | 100 : 1 | 100 |
| 7 | N-Benzylaminomethanediphosphonic acid | 2 | 1000 : 1 | 81 |

Table I-continued

Inhibition of the formation of a CaCO$_3$-precipitate by N-substituted aminoalkane-1,1-diphosphonic acids after 24 hours at 20°C

| Inhibitor No. | Inhibitor | Inhibitor amount × ml | Relative Molar Concentration of Ca$^{++}$ : Inhibitor | Ca-dissolved in % of total Ca |
|---|---|---|---|---|
| | | 6 | 1000 : 3 | 100 |
| | | 20 | 100 : 1 | 100 |
| 8 | N,N-Dimethylaminomethanediphosphonic acid | 6 | 1000 : 3 | 75 |
| | | 20 | 100 : 1 | 100 |
| 9 | Piperidino-N-methanediphosphonic acid | 6 | 1000 : 3 | 18 |
| | | 20 | 100 : 1 | 100 |
| 10 | N,N-Dibutylaminomethanediphosphonic acid | 20 | 100 : 1 | 30 |
| | | 30 | 100 : 1.5 | 100 |
| Blank test | | 0 | — | 11 |

EXAMPLE 2

In a procedure analogous to Example 1, 10 ml of a 0.1 molar CaCl$_2$ solution were reacted with an amount in ml of a solution of 0.5 m mols/l of the inhibitor, designated in Table 2 as $x$, and with 980−$x$ ml of freshly boiled and degassed distilled water. Subsequently 10 ml of a 0.1 molar Na$_2$CO$_3$ solution were added.

The blank test was prepared analogously, but without addition of precipitation inhibitor.

Both samples were maintained at 85°C for 24 hours and then cooled to 20°C. The effectiveness of the inhibitor was determined according to the procedure described in Example 1.

The results obtained are reproduced in Table 2. The inhibitors are designated by a number that correspondingly refers to the data in Table 1.

These results show that the effectiveness of the precipitation inhibitor compounds used according to the invention retain the same high degree of effectiveness at elevated temperatures above 40°C.

Table 2

Inhibition of the formation of precipitates of CaCO$_3$ by N-substituted aminoalkane-1,1-diphosphonic acid after heating for 24 hours at 85°C.

| Inhibitor No. | Inhibitor amount × ml | Relative Molar Concentration of Ca$^{++}$ : Inhibitor | Ca-dissolved in % of total Ca |
|---|---|---|---|
| Blank test | 0 | — | 33 |
| 1 | 4 | 1000 : 2 | 100 |
| | 20 | 100 : 1 | 100 |
| 2 | 4 | 1000 : 2 | 100 |
| | 20 | 100 : 1 | 100 |
| 3 | 4 | 1000 : 2 | 100 |
| | 20 | 100 : 1 | 100 |
| 4 | 4 | 1000 : 2 | 100 |
| 5 | 4 | 1000 : 2 | 100 |
| 6 | 4 | 1000 : 2 | 100 |
| | 20 | 100 : 1 | 100 |
| 7 | 4 | 1000 : 2 | 100 |
| | 20 | 100 : 1 | 100 |
| 8 | 4 | 1000 : 2 | 100 |
| | 20 | 100 : 1 | 100 |
| 9 | 4 | 1000 : 2 | 54 |
| | 20 | 100 : 1 | 100 |
| 10 | 4 | 1000 : 2 | 58 |
| | 20 | 100 : 1 | 84 |

EXAMPLE 3

In a procedure analogous to Example 1, the effectiveness of suitable alkali-metal salts and ammonium salts of N-substituted aminoalkane-1,1-diphosphonic acids was examined. The amounts of inhibitor utilized and the obtained detailed results are listed in Table 3.

The precipitation inhibitors are again designated by numbers that refer to the data in Table 1.

Table 3

Inhibition of the formation of a precipitate of CaCO$_3$ by disodium salts, dipotassium salts and diammonium salts of N-substituted aminoalkane-1,1-diphosphonic acids after 24 hours at 20°C.

| Inhibitor No. | Salt | Inhibitor amount × ml | Relative Molar Concentration of Ca$^{++}$ : Inhibitor | Ca-dissolved in % of total Ca |
|---|---|---|---|---|
| Blank test | — | 0 | — | 8 |
| 3 | Na$_2$ | 20 | 1000 : 1 | 96 |
| | K$_2$ | 20 | 100 : 1 | 98 |
| | (NH$_4$)$_2$ | 20 | 100 : 1 | 98 |
| 4 | Na$_2$ | 1 | 10000 : 5 | 100 |
| | Na$_2$ | 6 | 1000 : 3 | 100 |
| | K$_2$ | 1 | 10000 : 5 | 100 |
| | K$_2$ | 6 | 1000 : 3 | 100 |
| | (NH$_4$)$_2$ | 6 | 1000 : 3 | 100 |
| | (NH$_4$)$_2$ | 20 | 100 : 1 | 100 |
| 5 | Na$_2$ | 1 | 10000 : 5 | 100 |
| | Na$_2$ | 6 | 1000 : 3 | 100 |
| | Na$_2$ | 20 | 100 : 1 | 100 |
| | K$_2$ | 1 | 10000 : 5 | 100 |
| | K$_2$ | 6 | 1000 : 3 | 100 |
| | K$_2$ | 20 | 100 : 1 | 100 |
| | (NH$_4$)$_2$ | 6 | 1000 : 3 | 100 |

-continued

| Inhibitor No. | Salt | Inhibitor amount × ml | Relative Molar Concentration of $Ca^{++}$ : Inhibitor | Ca-dissolved in % of total Ca |
|---|---|---|---|---|
|   | $(NH_4)_2$ | 20 | 100 : 1 | 100 |
| 6 | $Na_2$ | 6 | 1000 : 3 | 100 |
|   | $Na_2$ | 20 | 100 : 1 | 100 |
|   | $K_2$ | 6 | 1000 : 3 | 100 |
|   | $K_2$ | 20 | 100 : 1 | 100 |
|   | $(NH_4)_2$ | 6 | 1000 : 3 | 100 |
|   | $(NH_4)_2$ | 20 | 100 : 1 | 100 |
| 8 | $Na_2$ | 6 | 1000 : 3 | 100 |
|   | $Na_2$ | 20 | 100 : 1 | 100 |
|   | $K_2$ | 6 | 1000 : 3 | 100 |
|   | $K_2$ | 20 | 100 : 1 | 100 |
|   | $(NH_4)_2$ | 6 | 1000 : 3 | 100 |
|   | $(NH_4)_2$ | 20 | 100 : 1 | 100 |

EXAMPLE 4

The tests according to Example 3 were repeated except that the samples were maintained at 85°C for 24 hours instead of being maintained at 20°C. In all cases a 100% prevention of the formation of a precipitate was found to result.

EXAMPLE 5

10 ml of a 0.1 molar solution of a soluble alkaline earth metal salt corresponding to the alkaline earth cation of the insoluble salts listed in Table 4 were treated with 60 ml of a 0.5 m mol/l solution of the trisodium salt of the N-methyl-1-aminoethane-1,1-diphosphonic acid and 920 ml of freshly boiled, degassed distilled water. Subsequently 10 ml of a 0.1 molar solution of the respective anion was added in the form of one of its soluble salts.

The blank test was prepared analogously, but without the addition of a precipitation inhibitor.

Both samples were maintained at 20°C for 24 hours. The degree of precipitation inhibition was determined according to the description in Example 1.

Table 4 shows the results thereby obtained. The molar proportions used in these four examples were chosen for reason of comparison and are not intended to be limitative of the minimum or maximum working concentrations. A 100% inhibition of the precipitation of calcium and barium sulfate can already be attained from the application of lesser amounts of inhibitors.

Table 4

| Salt | Relative molar concentration $Me^{++}$: Inhibitor | $Me^{++}$ dissolved in % of total $Me^{++}$ |
|---|---|---|
| $CaSO_4$ | 100 : 3 | 100 |
| $BaSO_4$ | 100 : 3 | 100 |
| $CaC_2O_4$ | 100 : 3 | 68 |
| $CaHPO_4$ | 100 : 3 | 100 |

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A process for inhibiting the precipitation of insoluble salts from aqueous solutions comprising adding to an aqueous solution containing a precipitable salt, a sequestering agent selected from the group consisting of (a) N-substituted aminomethane -1,1-diphosphonic acids having the formula

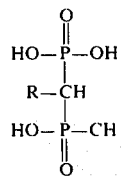

wherein R is a member selected from the group consisting of piperidino, morpholino, pyrrolidino, piperazino and

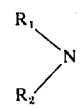

wherein $R_1$ is a member selected from the group consisting of alkyl having 1 to 6 carbon atoms, phenyl, phenylalkyl having 7 to 9 carbon atoms, alkylphenyl having 7 to 9 carbon atoms, cycloalkyl having 5 to 6 carbon atoms, pyridyl, and pyrrolyl; and wherein $R_2$ is a member selected from the group consisting of hydrogen and alkyl having 1 to 6 carbon atoms, (b) alkali metal salts of said acids, (c) ammonium salts of said acids, and (d) mixtures thereof, in a molar ratio of 5 × $10^{-4}$ to 5 × $10^{-2}$ mols of said agent per mol of precipitable salt cation in said aqueous solution.

2. The process of claim 1 in which the precipitable salt is selected from the group consisting of salts having alkaline earth metal cations and salts having iron cations.

3. The process of claim 1 in which the temperature of the solution is above 40°C.

* * * * *